United States Patent [19]

Moore et al.

[11] Patent Number: 5,247,555

[45] Date of Patent: Sep. 21, 1993

[54] RADIATION IMAGE GENERATING SYSTEM AND METHOD

[75] Inventors: Robert M. Moore; Nader Atari, both of Richmond, Va.

[73] Assignee: Nucletron Manufacturing Corp., Richmond, Va.

[21] Appl. No.: 696,009

[22] Filed: May 6, 1991

Related U.S. Application Data

[63] Continuation-in-part of Ser. No. 554,883, May 20, 1990, Pat. No. 5,132,996, which is a continuation-in-part of Ser. No. 264,112, Oct. 28, 1988, Pat. No. 5,014,290.

[51] Int. Cl.⁵ .............................................. H05G 1/64
[52] U.S. Cl. .......................................... 378/4; 378/25; 378/62; 378/99
[58] Field of Search ................. 378/44, 22, 6, 20, 190, 378/62, 196, 197, 205, 98, 99, 4, 19, 901, 24; 364/413.13, 413.12

[56] References Cited

U.S. PATENT DOCUMENTS

| | | | |
|---|---|---|---|
| 4,624,007 | 11/1986 | Muranushi | 378/4 |
| 4,674,046 | 6/1987 | Ozeki et al. | 378/901 |
| 4,702,257 | 10/1987 | Moriyama et al. | 378/4 |
| 4,833,698 | 5/1989 | Flannery et al. | 378/19 |
| 4,852,137 | 6/1989 | Mackay | 378/62 |
| 4,872,187 | 10/1989 | Nakahata et al. | 378/4 |
| 4,922,512 | 5/1990 | Lajus et al. | 378/197 |
| 4,974,249 | 11/1990 | Zweig | 378/190 |
| 5,014,290 | 5/1991 | Moore et al. | 378/4 |
| 5,027,380 | 6/1991 | Nishiki | 378/4 |
| 5,060,246 | 10/1991 | Van der Brug et al. | 378/24 |
| 5,127,032 | 6/1992 | Lam et al. | 378/65 |

*Primary Examiner*—David P. Porta
*Assistant Examiner*—Kim-Kwok Chu
*Attorney, Agent, or Firm*—Millen, White, Zelano, & Branigan

[57] ABSTRACT

A radiation image generating system for providing planar and tomographic views of portions of a patient's anatomy for use in radiation therapy procedures comprises a fluoroscopic simulator apparatus having a radiation source; a computer system for acquisition and processing of radiation transmission images; a manual input; display and storage devices for such images; means for simulation of an irradiation beam; and, apparatus for the cutting of blocker contour templates, blocker patterns and blockers. The system provides planar transmission images and tomographic views associated and correlated therewith. The system's radiation image detecting means includes an area solid state camera having a planar detector array that is cooled below ambient temperatures. The system further includes means for passively converting radiation transmission images into light images for detection by the camera. The system and method of the invention can provide a plurality of tomographic views from a rotational scan of the patient and it can provide three-dimensional in-depth views that can be displayed also while being rotated about an axis.

32 Claims, 6 Drawing Sheets

RADIATION IMAGE GENERATING SYSTEM AND METHOD

This application is a continuation-in-part application of copending U.S. application Ser. No. 554,883 filed May 20, 1990, now U.S. Pat. No. 5,132,996 issued Jul. 21, 1992, and entitled "Simulation/Generation/Verification System for Radiation Therapy Blockers," which, in turn is a continuation-in-part application of Ser. No. 264,112, filed Oct. 28, 1988, of the same title. (Now U.S. Pat. No. 5,014,290 issued May 7, 1991.) Both of said applications are incorporated herein by reference.

BACKGROUND

This invention relates to apparatus and a method for generating radiation images for use in radiation therapy. In particular, it relates to passive conversion of X-ray transmission images into light images. The invention also relates to the detection of such images by a cooled, solid-state camera, and to the acquisition, storage, and processing of the obtained images by a computer. The invention also relates to the generation of planar images and coordinated tomographic views; the generation of three-dimensional in-depth views; the simulation of irradiation beams and blocker silhouettes; and, to the fabrication of radiation blockers.

A variety of devices are presently used in radiation therapy procedures for producing so-called blockers (masks) of radiation-impermeable or radiation attenuating materials for masking radiation of all but specifically designated body areas. Conventionally, a patient is positioned in a radiographic simulator that produces real-time X-ray images and X-ray films. Under fluoroscopy conditions, a physician positions field-defining wires in the simulator to outline the desired target area and one or more x-ray films are exposed to show the entire field including the superposed field-defining wires. The patient is then dismissed and x-ray films are developed. Thereafter, the target area is manually marked on the film further to define the designated area for irradiation. Also compensator contours can be defined for generation of compensator filters.

A blocker pattern is then conventionally produced from a sheet of polystyrene foam material by manual tracing the target area (intended blocker) silhouette or contour marked on the x-ray film. This is performed in an apparatus that cuts a polystyrene foam block in appropriately scaled-down, silhouette outline along lines (rays) originating at the origin of radiation. The foam block is conventionally cut by a heated wire or by a milling machine. A compensator filter pattern may also be produced for use in conjunction with such a blocker pattern. Thusly obtained patterns are further utilized for the casting of blockers (masks) and compensator filters from appropriate radiation-impermeable or radiation-attenuating alloys.

A cast blocker and a compensator filter are eventually inserted and aligned in the radiation path of a radiation therapy apparatus, as for instance represented by cobalt sources or by linear accelerators and the like. Before treatment commences, a blocker is sometimes verified for its accuracy and alignment either in a radiographic simulator or in the actual radiotherapy apparatus (while the patient is aligned therein).

Such radiotherapy simulators are marketed in the U.S.A., for example, by the Varian Company, Palo Alto, Calif., under the name Varian Ximatron C-series Radiotherapy Simulators, and by the Kermath Manufacturing Corporation, Richmond, Va., under the name Kermath Radiographic Fluoroscopic Simulator. The Kermath Manufacturing Corporation also manufactures computer assisted tomographic (section scanning) apparatus. A Kermath T.O.P. 2000 System is used, for example, in radiotherapy simulation. Similarly, the Portalcast Block Casting System by Diacor, Salt Lake City, Utah, is a heated-wire, cutting apparatus for blocker patterns and casting apparatus for the casting of blockers.

Whereas prior-art systems for the provision of blockers are in many ways satisfactory, the involve procedures are relatively cumbersome, time consuming, and are subject to human error and to errors due to inaccuracies of existing equipment. For instance, the patient must make a special visit to a facility specifically only for initial determination of the radiation target area or field (after which the patient is dismissed). There is then a consequent need for processing of X-ray film and marking of target outline thereon; and, the need for subsequent cutting of the blocker pattern and casting of the actual blocker before the blocker may be verified (in advance of treatment). This requires another special visit by the patient which is time consuming and costly, and detrimental to the patient's tranquility. Moreover, the described procedure may need to be repeated, if verification shows the blocker to be inaccurate.

In view of the required steps and passage of time between steps (commonly amounting to at least several days), errors occur not only due to accuracy limitations of equipment and human failing, but also, for example, because of changes in the size, shape and position of tumors. In this respect, manual marking of target outlines on an x-ray film and the subsequent manual tracing of such outlines on a blocker pattern cutting apparatus contribute to the incidence of inaccuracies and errors.

Radiographic simulators employed in the past in procedures such as those described in the foregoing have relied upon generating X-ray transmission images of a patient's anatomy for direct viewing upon a flouroscope screen and/or by exposing photographic film thereto. In order to improve images and to reduce patient exposure to radiation, fluoroscopic screen images have been intensified in active image intensifiers and, further, video cameras and electronic image-grabbing and processing by a digital computer have been employed. Additionally, computer processing of radiation transmission image information has provided tomographic views to further improve accuracy, speed, convenience, and the like of radiographic simulation procedures.

Such improvements and prior art relating thereto have been disclosed and described in U.S. Pat. No. 5,014,290 and copending continuation-in-part application Ser. No. 554,883, filed Jul. 20, 1990.

Additionally, U.S. Pat. No. 4,872,187 discloses a system for inspection of minute defects in industrial parts. That system comprises an image intensifier, a linear image sensor of the charge storage type for providing tomographic images, and a light path change-over mechanism for introducing a two-dimensional output image of the image intensifier into an image pick-up tube to provide planar images.

Complexity of equipment, speed of operation, resolution and accuracy of obtainable images, and the like are matters that are of importance. For instance, an active image intensifier apparatus and a cathode-ray type camera necessarily involve considerable equipment complexity as well as image distortions and inaccuracies. For practical reasons of size (and cost) of active image intensifiers, thusly obtained images are limited in size to only a portion of the coverage area desired and conventionally provided by X-ray film in simulation procedures of concern here. Consequently, a number of such image portions have had to be assembled to provide images of adequate coverage. The latter clearly adversely affects speed of operation and accuracy. It also increases radiation exposure of the patient. Radiation exposure of the patient, however, needs to be kept as low as possible, yet sensitivity of image detection and resolution of obtained images are generally directly a function of the used radiation intensity.

Also, the provision of tomographic views in addition to planar images contributes significantly to the accuracy of irradiation simulation and verification procedures; and, such accuracy is enhanced if the number of correlated tomographic views is increased. However, in the past, each tomographic view has required a separate rotational scan of multiple images from different angles about a patient. Hence, the higher the number of tomographic views provided, the higher was the patient's exposure to radiation. Also, as each rotational scan requires a significant time, speed of acquisition of tomographic image information for multiple tomographic views has been correspondingly slow. Moreover, immobilization of a patient throughout multiple rotational scans is an additional problem.

In view of the foregoing, it is a feature of the present invention to provide improved apparatus and a method for providing relatively high-resolution, accurate planar and tomographic views, as well as 3-dimensional in-depth views of a patient's anatomy at relatively low radiation exposures. In this respect, radiation transmission images are passively converted to corresponding light images that are detected by a cooled planar detector array in a solid state camera. During a rotational scan about a patient at relatively low radiation exposure, the light images are then able to be grabbed and further processed by a digital computer to obtain tomographic information for the construction and simultaneous display of a plurality of different tomographic views and for the construction of 3-dimensional, in-depth views.

SUMMARY

In accordance with principles of the present invention, a patient is appropriately positioned within an X-ray imaging apparatus and X-ray transmission images of specific body regions are converted to corresponding light images in a passive image converter. The passive image converter utilizes a phosphorescent screen for the conversion. The light images are viewed by a solid state video camera whose planar array of detectors is cooled below ambient temperatures to improve charge storage integration capability of the detectors and to increase the signal-to-noise ratio of the obtainable electronic image signals. The planar array comprises charge coupled devices ("CCD"). The detected light images are converted in the camera to electronic image signals which are acquired or grabbed by conventional computer equipment. The grabbed images are processed and stored in the computer and are displayed on monitor screens. Displayed images can include planar views, tomographic views, and 3-dimensional, in-depth views.

For the purpose of this description, "three-dimensional, in-depth views" are intended to include isometric and perspective views of a transparent character so that internal structure is revealed.

The optical path between the passive image converter and the camera is folded at a right angle by an interposed mirror. This avoids exposure of the camera to X-rays.

While planar images are acquired by the system, the iso-center axis from the X-ray source and through a center of the patient's anatomy to be imaged intersects the image plane area of the passive image converter substantially centrally. While tomographic view information is acquired, the iso-center axis intersects the image plane area substantially in a peripheral location thereof.

The system further includes means for receiving manual operator inputs to its computer with respect to radiation blocker information for the superpositioning of blocker projection and intersection outlines with the obtained planar and tomographic views onto displayed views. This information permits interactive manipulation of such outlines to obtain the desired blocker shapes and sizes and for proper positioning thereof in relation to the images. Additionally, an embodiment of the invention provides for the generation of cutter signals and for the cutting of blockers or blocker patterns under computer control.

The following describes typical use and operation of the system of the present invention. The attending physician/oncologist manipulates displayed images via appropriate computer inputs and traces the outline of the target field (for eventual irradiation) on the display screen by means of conventional computer accessories such as, for example a light pen or a mouse. Once a satisfactory target contour is overlaid on the image, it and the image are recorded together. At this time, a blocker-pattern cutting device (controlled by the computer) cuts a blocker paragon in the form of a blocker contour template or a blocker pattern (of the target contour) from a blank of an appropriate material (for instance styrofoam or other material) in accordance with the recorded overlay image. For example, a styrofoam blank is precoated or preimpregnated with barium or the pattern itself is treated with barium subsequent to cutting, so that the pattern becomes at least partially opaque to X-rays. Other precoating or postcoating can include impregnation or coating with aluminum or other partially-opaque materials.

The template or blocker pattern is then placed in proper registration within the fluoroscopic apparatus as a mask in front of the x-ray source and the x-ray facility of the apparatus is used to verify registration, alignment and accuracy of the cut contour in relationship to the patient (who remains conveniently positioned in the apparatus). Images obtained and prior images are superposed, or compared side-by-side, or otherwise manipulated in various conventional ways; and, such overlay images are recorded and stored. X-ray film of the verification (overlay) images may then be taken for record purposes.

Successful verification of a blocker template is consequently followed by the automatic cutting of the actual blocker pattern in conformance with substantially the same computer-cum-cutting-device set-up as had been used to cut the template. Alternately, if the step of cutting and verifying of a template is omitted, a blocker pattern per se is cut and verified. In either case, adequate verification has been performed.

A blocker pattern that has been verified (by itself or by its template) is then ready to be used in a conventional blocker casting process that provides an actual blocker from radiation-impermeable or radiation-attenuating alloy within less than one half hour. Thereafter, the blocker is inserted in appropriate position in a radiation therapy apparatus to more accurately shield all but those patient body areas required to be irradiated. The blocker may include a compensator filter for detailed relative radiation dosage compensation (attenuation) in different regions of the target area.

As hereinbefore indicated, a blocker pattern is produced, for example, by the cutting of a styrofoam blank. This cutting operation may be performed, for instance, in a conventional heated-wire cutting device or by a special milling cutter device, but whose cutting operation is automatically controlled, according to principles of the present invention, by a computer in accordance with the stored overlay images.

The radiation image generating system and the method of the invention are capable of providing planar images corresponding to X-ray transmission images and tomographic views that are computer-constructed from multiple X-ray transmission images viewed by the camera from different angles during relative rotation between a patient and the equipment. Moreover, tomographic information to provide a plurality of different tomographic views can be obtained by rotation of the equipment about the patient. Furthermore, multiple planar transmission images are viewed by the camera from a plurality of directions during a relative revolution between a patient and the equipment to provide three-dimensional in-depth volume information of the imaged portion of the patient's anatomy. This information is then utilized by the compute to reconstruct tomographs along any desired plane. Additionally, even during rotation, display monitors can show three-dimensional, in-depth images that can be viewed from any direction.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference numerals refer to like parts throughout the different views. The drawings are schematic and not necessarily to scale, emphasis instead being placed upon illustrating principles of the invention.

DESCRIPTION OF THE PREFERRED EMBODIMENTS

Figure 1:
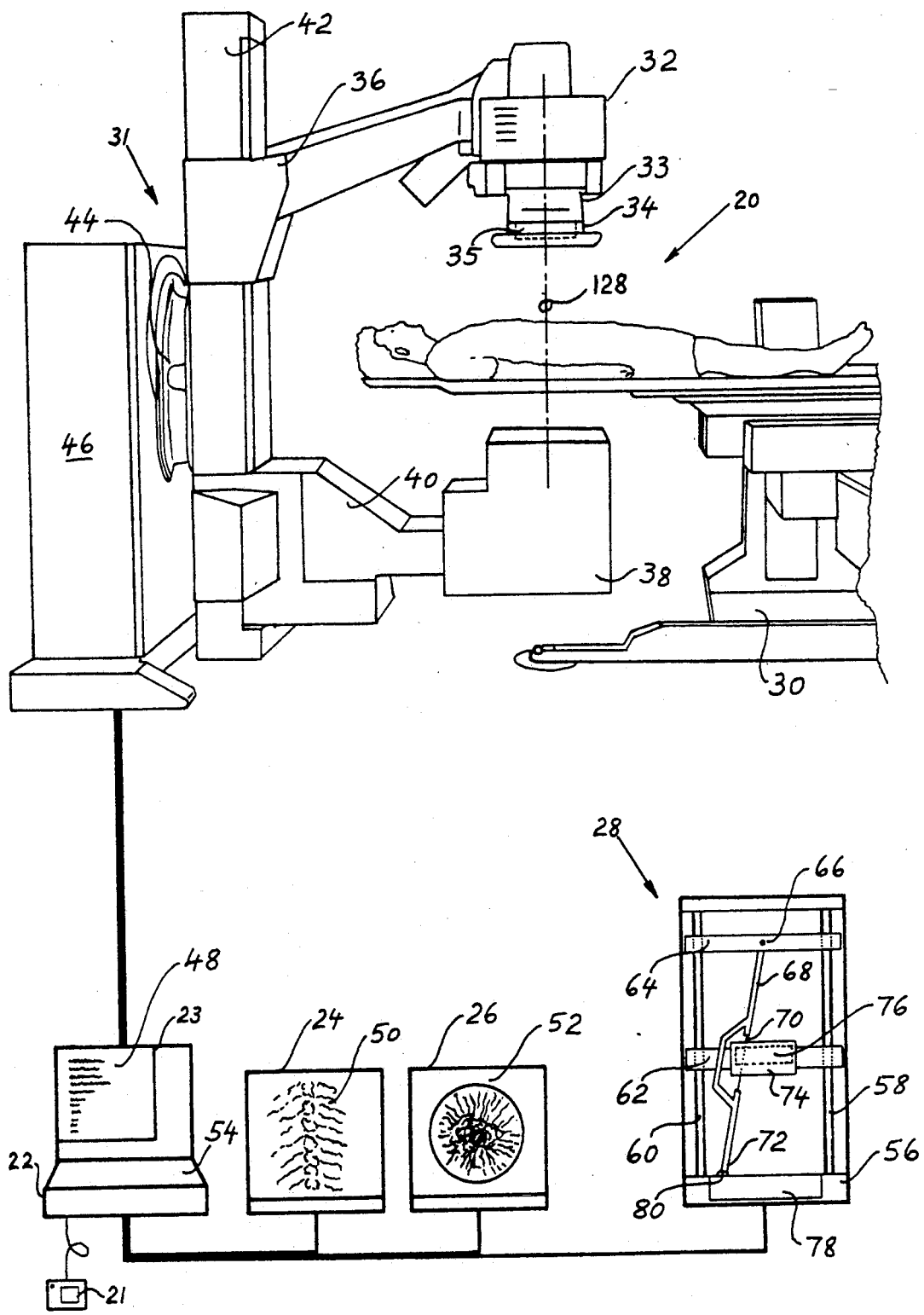
FIG. 1 is a schematic, composite, frontal view of a simulation/verification system for radiation therapy blocker patterns and/or blockers.

Referring now to FIG. 1 a fluoroscopic simulator 20 is shown in the upper half of the drawing. A computer 22, having a computer display 23, is connected to simulator 20 via an electrical cable. First and second monitors 24 and 26 are connected to computer 22 for the display of images and a mouse 21 (or a light-pen or similar arrangement) is connected to computer 20 for image control functions such as manipulation or the generation of image-superposition contours. Computer 20 is further connected to a cutting device 28.

Simulator 20 includes a table arrangement 30 to support and align a patient in appropriate position for fluoroscopy and tomographic scanning. A fluoroscopic device 31 comprises an x-ray head 32 that is disposed in an adjustable cantilevered, manner on a carriage 36; an image detecting assembly 38 disposed in an adjustable cantilevered manner on a support 40; and, a track pillar 42 along which carriage 36 and support 40 are independently adjustably carried. Image-detecting assembly 38 commonly also incorporates x-ray film holder and exposure arrangements. Track pillar 42 is mounted on a rotary drive mount 44 which, in turn, is mounted on a support base 46. This mechanism can be adjusted to any position or rotated about a patient. X-ray head 32 includes a horn 33 which incorporates a field mask section 34 for holding various field-defining devices. The head 32 also includes a blocker tray holder 35.

Computer 22 includes a keyboard 54 and a display 23 with a terminal screen 48. Although not shown, computer 22 further comprises conventional components, including recording and storage devices, output devices such as printers and plotters and the like. Terminal screen 48 and monitors 24 and 26 can be used interchangeably. In general, however, screen 48 is used to display text; monitor 24 is used to display fluoroscopic images and composites thereof; and, monitor 26 is used to display tomographic section images. Monitor 26 can also be used to display three-dimensional, in-depth views. Further monitors may be present to display additional information or images.

Cutting device 28 comprises a blocker-pattern cutter of a conventional kind. It is modified according to principles of this invention, however, to facilitate automatic contour cutting under control of computer 22.

Basically, cutting device 28 comprises a housing having disposed therein a cutter base 56, a pattern carriage 62, and a pivot carriage 64. Carriages 62 and 64 are adjustably mounted upon first and second rails 58 and 60. Pivot carriage 64 comprises a pivot 66 (of a ball-joint kind) to which a cutter bar 68 is attached such that cutter bar 68 is free to pivot at pivot 66. A guide end 72 is provided at the lower end of cutter bar 68. Along its length, cutter bar 68 has a bow-like section to by-pass pattern carriage 62 and a shunt portion including a heated wire 70 for cutting blanks such as those made of styrofoam. Pattern carriage 62 comprises a pattern mount 74 which holds such styrofoam material while it is being cut by heated wire 70. The styrofoam material or the resulting pattern is indicated schematically by the outline of a blocker pattern blank 76.

Cutter base 56 is provided with a motorized two-axis positioner 78 which engages guide end 72 of cutter bar 68. For this purpose, a ball-joint connector 80 is disposed on positioner 78 such that guide end 72 is securely guided along both horizontal axes (by positioner 78) while cutter bar 68 is angularly moved about pivot 66. Cutter bar guide end 72 telescopes within the ball-joint connector during such motion or cutter bar 68 itself telescopes.

Conventionally, unmodified, manually operated cutting devices are provided with a light table within cutter base 56 (in place of two-axis positioner 78) upon which x-ray film is placed so that desired blocker contours can be manually traced by moving the guide end 72 by hand. In accordance with principles of the present invention, however, the operation of the motorized two-axis positioner 78 is connected to and controlled directly by computer 22. Motorized two-axis positioner 78 is of a conventional type.

Figure 2:
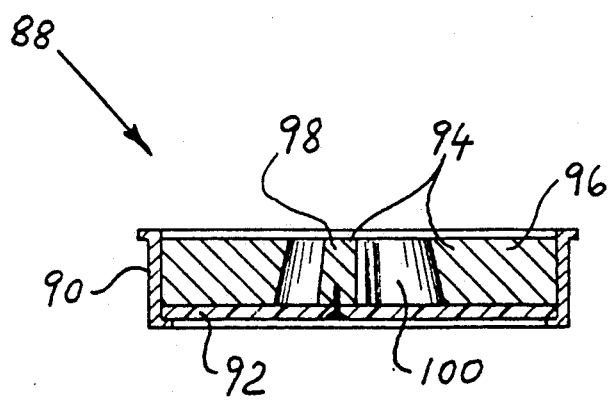
FIG. 2 is a schematic, sectional view of a blocker-holding arrangement.
Figure 3:
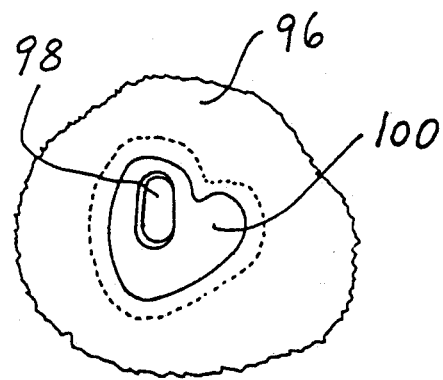
FIG. 3 is a schematic, fragmental, partial top view relating to the depiction shown in FIG. 2.

Referring now to FIGS. 2 and 3, a conventional blocker (or blocker pattern) holding arrangement 88 includes a blocker tray 90 within which a plastic tray plate 92 (usually of acrylic) is securely supported. A blocker 94 is disposed upon the tray plate 92. Blocker 94 comprises at least a blocker body 96, but also may comprise one or more islands as indicated by a blocker isle 98 disposed within a contoured, unobstructed region 100 fastened in position on tray plate 92 by a screw or a pin. The blocker isle 98 may be secured onto plate 92, however, in other conventional ways. Blocker holding arrangement 88 may also be of different structure, for instance, to suit different equipment makes. In accordance with the present invention, the blocker holding arrangement 88 and blocker tray 90 may also serve to hold a blocker template or a blocker pattern during verification. It should be understood that a blocker pattern is an inverse or negative of a blocker in order to serve as a mold for the casting of such a blocker. Blocker patterns are generally of polystyrene foam material and actual blockers are conventionally fabricated by casting (using blocker patterns as molds) from low-melting-temperature, high-density alloys that are radiation-impermeable or radiation-attenuating.

Blocker holding arrangement 88 is suited for insertion into blocker-tray-holder 35 in x-ray head 32 (FIG. 1) for verification of a blocker paragon, i.e. blocker 94 or a blocker template or a blocker pattern. Arrangement 88 can also be used for insertion into an appropriate location in a radiation treatment machine for verification purposes and for the actual irradiation process (in the latter case only a final blocker is applicable).

When the blocker 94 (or a blocker pattern) is appropriately positioned, an unobstructed region 100 is provided with tapering sidewalls at angles that are the same as angles of x-rays tangent thereto and originating at the point of origin of the radiation source of the fluoroscopic apparatus and the radiation treatment machine.

Blocker patterns are conventionally fabricated or cut for the purpose of providing patterns and cores for molds for casting of the actual alloy blockers, as hereinbefore indicated. Such conventional blocker patterns are not verified before casting of alloy blockers. Cast alloy blockers are sometimes verified in simulators, or, more commonly, in actual radiation treatment equipment by exposure of x-ray film through a blocker inserted into the equipment and by manual overlay over the original film that is marked up with a blocker contour. Sometimes such a verification (a so-called "port verification") also includes further x-rays of the patient with and without interposition of the alloy blocker. In any case, if only finished blockers are verified, the costly and cumbersome procedure lacks precision and, if a blocker is rejected, the entire blocker-generating process has to be be repeated. If blockers are not verified, significant danger and risk can be involved in radiation-treatment error due to the incidence of misaligned or misshapen blockers.

The present invention, however, facilitates immediate generation, fabrication, and verification of a blocker pattern while the patient is still aligned within the fluoroscopic simulator 20. According to principles of this invention, styrofoam blocker patterns are treated so that they become slightly opaque to x-rays such that they may be verified fluoroscopically without blocking the image entirely. This is achieved by precoating or preimpregnating of the blocker pattern blank either on its upper or on its lower surface (or on both surfaces) with barium or appropriate barium salt solution (or with other suitably partially radiation-opaque materials). Alternately, such coating or impregnating is performed subsequent to the cutting of the pattern.

The present invention also facilitates immediate generation, fabrication, and verification of a blocker template that is a substantially two-dimensional version of a blocker pattern and that facilitates verification of a computer-processed and stored blocker contour. The invention permits time to be saved in the cutting of such a template and in its handling during verification on the fluoroscopic apparatus. This is because the template comprises only a single piece of sheet material of relatively small thickness, whereas fabrication and preparation of a blocker pattern for verification purposes generally involves the handling and alignment of more than one pattern component with a thickness of several inches. Blocker template fabrication and verification will be described hereinafter in further detail.

Other cutting devices can be employed instead of the cutting device 28. For instance milling cutters, laser cutters, and the like are also suited to the task.

Figure 4:
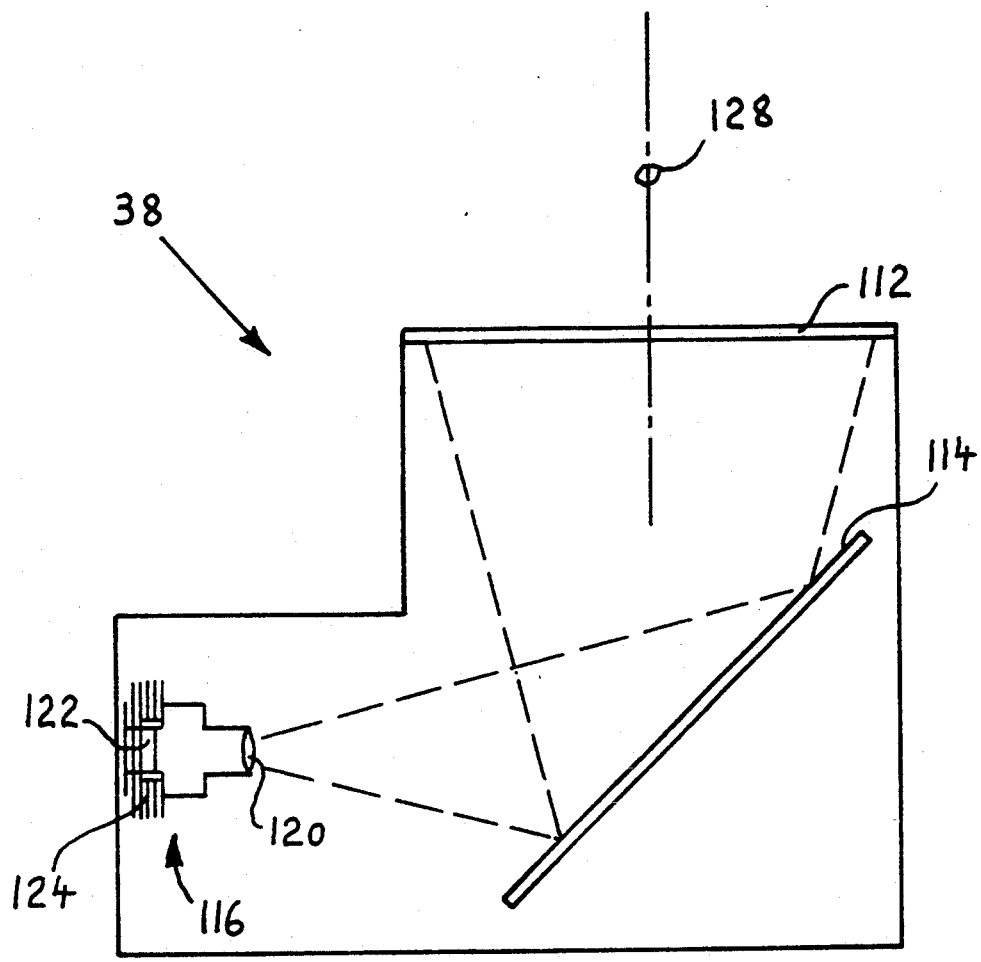
FIG. 4 is a schematic depiction of a radiation image detector assembly in FIG. 1.

FIG. 4 schematically shows the image detecting assembly 38 which includes a radiation image converter 112, a mirror 114, an area solid state video camera 116 of a charge coupled type, and a light-proof housing 118.

Image converter 112 is of a passive kind. It converts an X-ray transmission image into a planar light image; and, the conversion is accomplished only by virtue of the x-ray transmission image being projected onto the converter 112 from above. As shown, the converted image can be viewed from beneath the converter by camera 116. No electrical power is required for this conversion. Converter 112 includes a phosphorescent screen as the active element. A preferred active image area of the converter is 18×18 inches. This image area is substantially larger than the image area provided in customary equipment which is generally limited to a 12" diameter face of the implied conventional active image converter/intensifier. Hence, the present invention facilitates very significant increased image field coverage (with respect to the patient). This area increase also reduces significantly the time required for positioning of a patient. In this respect, converter 112 is of a conventional commercially-available kind that is generally employed for photographic X-ray film camera equipment as so-called intensifying screens. One such converter, for example, is available from Kodak and described in the literature as "Kodak Lanex Fast Screen", Catalog Number 116 0688. Other compatible commercial screens can also be used.

Mirror 114 is a high-quality first surface mirror and is oriented substantially at 45 degrees to the image-plane of the planar light image in the lower surface of converter 112.

Area solid state camera 116 comprises a lens 120, a planar array 122 of charge coupled devices (CCDs), and cooling means 124 for the array 122. Cooling means 124 is employed to reduce the temperature of the CCDs below ambient temperatures. In a preferred embodiment, for instance, the CCDs are cooled to minus 25 degrees C. Cooling means 124 can be of any conventional kind, but a preferred embodiment employs a solid state (Peltier effect) device with external, air-convection cooling fins. The advantage of cooling the array 122 includes a higher signal-to-noise ratio of video signals provided by the array and improved charge integration to obtain improved video signal levels. One such suitable camera 116 is commercially available in the U.S. from Photometrics Corporation of Arizona. Such a Photometrics camera is identified and described in the literature as a type CH250/A camera head.

In the above regard it has been previously suggested that intensified charge injection device (CID) cameras and intensified CCD cameras be used in digital real-time x-ray fluoroscopic systems. See, for example, page 862 et sec. of the Nov./Dec. 1989 issue of Medical Physics (Vol 16, #6) for a related article by one of the instant inventors. The results of the instant invention, however, are accomplished without such intensification; and, the prior article did not contemplate the use, for example, of the multiple-slice concepts described herein.

In operation of the image detecting assembly 38, an X-ray transmission image projected onto converter 112 (from above) is converted to a planar light image that is viewed (at the lower surface of the converter) via lens 120 by camera 116. The optical path between converter 112 and camera 116 is folded substantially orthogonally by mirror 114. This arrangement avoids significant exposure of the camera to X-rays that pass through converter 112.

An iso-center axis 128 in FIG. 4 is oriented orthogonally to the plane of the converter 112 and intersects the converter substantially centrally in the view shown. Iso-center axis 128 (as also indicated in FIG. 1) extends through the point of origin of the X-ray source in X-ray head 32, through the center of the patient's anatomy that is to be imaged, and on through the converter 112. When the system is operative in acquiring planar images (port images) directly corresponding to X-ray transmission images, iso-center axis 128 intersects the image-plane area of converter 112 substantially centrally. When the system is operative in acquiring image information for construction of tomographic images or for acquisition of 3-dimensional in-depth image information, the image detecting assembly 38 is preferably repositioned in respect to the iso-center axis 128 so that axis 128 intersects the image-plane area of converter 112 at a more peripheral portion. In this respect, in FIG. 4, this peripheral location is either behind or in front of the plane of the drawing.

In operation, a patient is appropriately aligned upon table arrangement 30 and fluoroscope device 31 is aligned with respect to the patient. Planar transmission images are projected onto converter 112 and converted therein to light images which are received by camera 116 and converted therein to electronic image information signals. The electronic image signals are grabbed by the computer and further processed and/or stored therein. The computer then reconstructs the planar light images for display, for example, by monitor 24 or 26.

In order to obtain tomographic views or 3-dimensional in-depth views, fluoroscope device 31 is again appropriately aligned and the image detecting assembly is repositioned with respect to iso-center axis 128, as hereinbefore discussed. Track pillar 42 is rotated by and about rotor drive mount 44 about an axis that intersects the center of the patient's anatomy to be viewed. Successive planar images are then grabbed by the computer at different angles of the rotation.

The computer-grabbed image information is conventionally stored and processed for reconstruction and display of various views. For example, the computer can reconstruct planar views as viewed from any angle of the equipment rotation. More importantly, by the use of conventional techniques, the computer constructs a plurality of different tomographic views through the patient's anatomy along any desired section plane, particularly along different and spaced apart section planes that are oriented more or less orthogonally to the axis of rotation of the equipment while the successive planar images have been grabbed by the computer. In this respect, one of the plurality of tomographic views can be in a section plane that is orthogonal to the axis of rotation and the other tomographic views can be in section planes whose angular orientations differ only minimally or insignificantly from orthogonality in relation to this axis of rotation. Furthermore, because computer-grabbed image information during the rotation includes in-depth three-dimensional information of the respective portion of the patient's anatomy, the computer uses the same conventional techniques to reconstruct three-dimensional, in-depth views of the anatomy from any viewing direction. Hence, such views can be displayed from any chosen viewpoint while being revolved about any desired axis.

Figure 5:
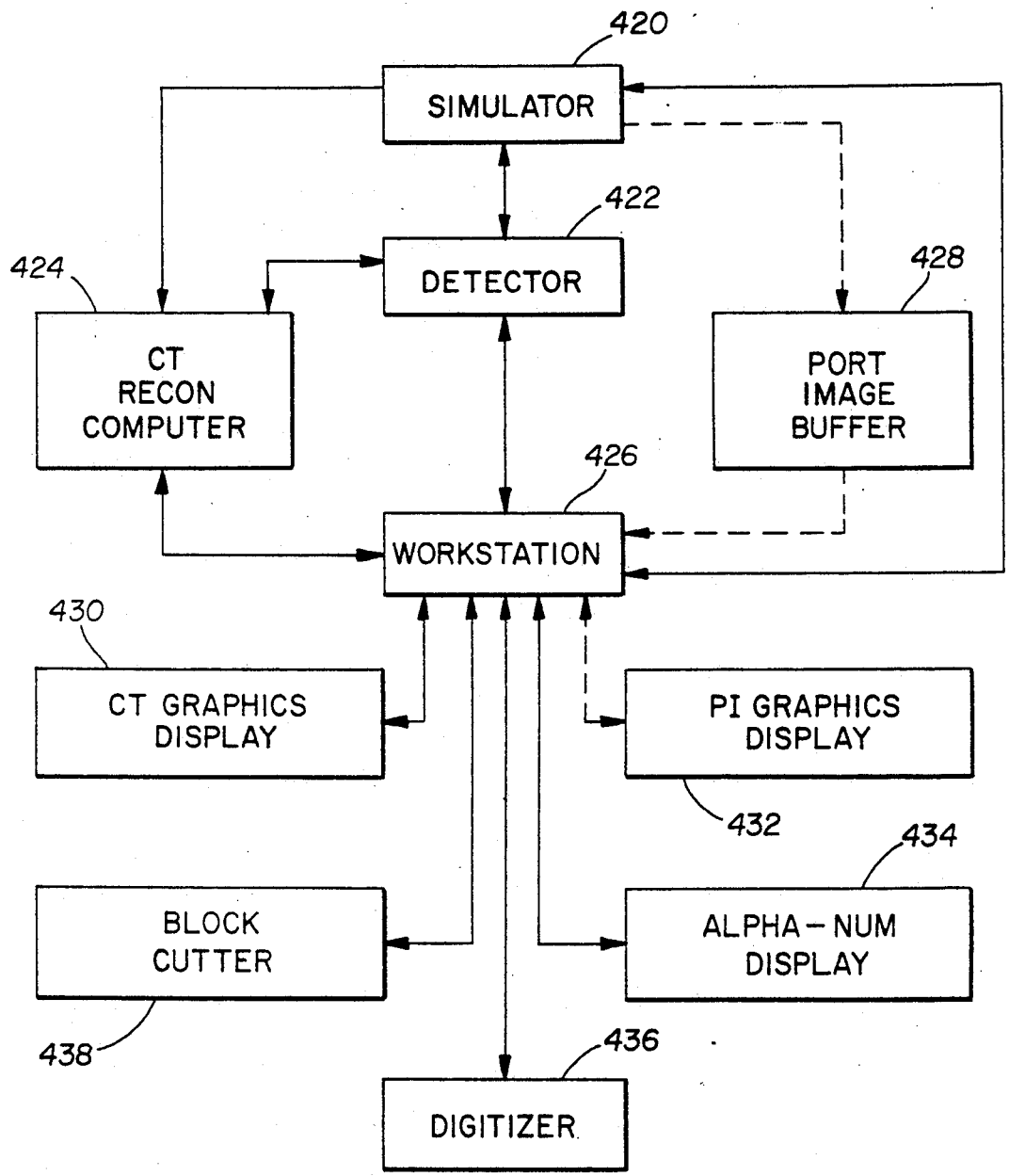
FIG. 5 is a schematic block diagram of principal components and respective functional interconnections employed in an embodiment of the invention.

The computer means for constructing the described tomographic and three-dimensional in-depth views comprise computer memory storage and appropriate programming and control mechanisms. Inasmuch as these structures and techniques are quite conventional, however, they will not be discussed in detail. The block diagram of FIG. 5, however, indicates an example of principal components and respective functional interconnections included in the system of the invention. The shown system includes a simulator apparatus 420, that is substantially representative of the fluoroscope device 31 (FIG. 1), but that now specifically includes a solid state detection member 422. FIG. 5 further illustrates interrelationships between important subsystems, as already given in foregoing descriptions.

As described in more detail in copending application Ser. No. 554,883, tomography reconstruction computer 424 interconnects with a suitable detection member 422 and further communicates with a simulator apparatus 420 and a computer work station 426—these structures corresponding to FIG. 1 elements 22, 38, 20, and 22, respectively. Reconstruction computer 424 also serves for reconstruction of three-dimensional in-depth images (and rotation thereof). Computer work station 426 also communicates with simulator apparatus 420 and also specifically with detection member 422. Although solid state detection member 422 can (and does) provide planar port image input to computer work station 426 (in addition to providing tomography input to tomography reconstruction computer 424), computer work station 426 can alternately or additionally receive a planar port image directly from simulator apparatus 420. The latter planar port image can be provided via a port image buffer 428, as indicated by dashed interconnection lines.

Connected with or part of the computer work station 426 are the indicated tomographic and 3-d display unit (or units) 430 (corresponding to elements 24 and 26 in FIG. 1), port image display unit 432, alpha-numeric display unit 434, and a digitizer unit 436 (mouse, trackball, lightpen, graphic tablet, or the like). A block cutter 438 (corresponding to 28 in FIG. 1) is shown here also in communication with computer work station 426.

Figure 6:
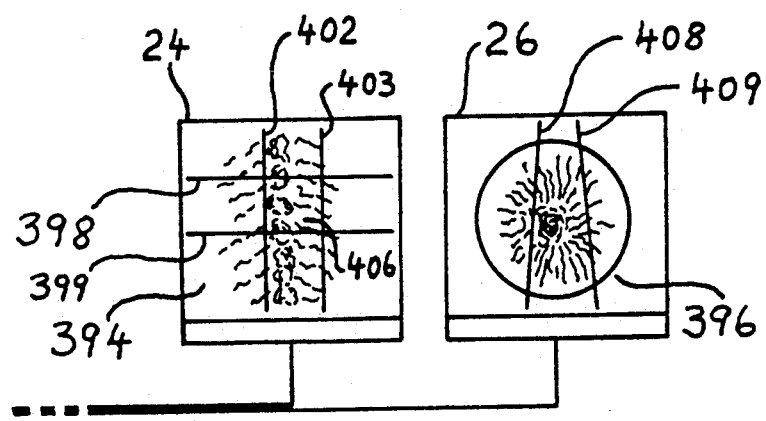
FIG. 6 is a schematic representation of an example of coordinated image displays.

Referring now to FIG. 6, first and second monitors 24 and 26, as they are connected to computer 22 in the system shown in FIG. 1, are depicted displaying a planar image 394 and a tomographic image 396, respectively. Computer-generated and via computer-inputs manually-adjustable field-delineating lines are optionally displayed overlaid over planar image 394 to facilitate the definition of an irradiation target field by medical personnel. These field-delineating lines are shown here in the form of horizontal delineators 398 and 399 and vertical delineators 402 and 403, to define therebetween a field 406. Field 406 corresponds to an intersectional outline of an irradiation beam simulation with a portion of a patient's anatomy that is represented by planar image 394. Images 394 and 396 are mutually coordinated in that tomographic image 396 shows a tomographic section (section plane is horizontal with respect to planar image 394) through a body portion displayed by planar image 394, in particular in a location disposed within field 406 or in close vicinity thereof.

Computer-generated irradiation-beam delineating lines are displayed overlaid over tomographic image 396 to facilitate visualization of intersectional outlines of an irradiating beam (irradiating beam simulation) in its path through a body portion as represented here by tomographic image 396. These beam delineating lines are adjusted and updated by computer 22 (FIG. 1) to correspond to the respective irradiating beam simulation outline defined by field 406 in planar image 394. Moreover, these beam-delineating lines (in tomographic image 396) are also adjusted and updated by computer 22 whenever a different tomographic section is chosen by the operator for display. Additionally, these beam delineating lines are also automatically readjusted and updated by computer 22 whenever field 406 is manually readjusted. These beam-delineating lines 408 and 409 (in tomographic image 396) represent intersection outlines between an irradiating beam simulation (that corresponds to field 406) and the tomographic slice shown in tomographic image 396.

Beam delineators 408 and 409 are downwardly divergent in correspondence with the divergence of an irradiating beam that generally originates substantially in a point source and passes through an opening corresponding to field 406. In this respect, it will be understood that beam delineators 408 and 409 can become joined in the shape of a truncated angle outline in situations where a coordinated tomographic image is chosen for display and viewing to represent a section along a horizontal line (in planar image 394) which is vicinally disposed above or below field 406.

It will be appreciated that the described coordinated delineator generation and display provides a powerful tool for medical personnel more exactly to define regions for irradiation and to reduce or avoid undesirable or superfluous irradiation of body portions. This is provided by the hereinabove described embodiment's capability of simulating and displaying a manually preselected and adjusted intersection outline of an irradiating beam simulation with a planar x-ray image; and, by simulating and displaying the intersection of the irradiating beam simulation with a tomographic section. In this manner, the structure and method of the invention provide in-depth, substantially three-dimensional irradiation exposure simulation information. This capability contributes significantly to a more exact targeting of irradiation and to avoidance of radiation exposure of body regions which do not require irradiation treatment.

Figure 7:
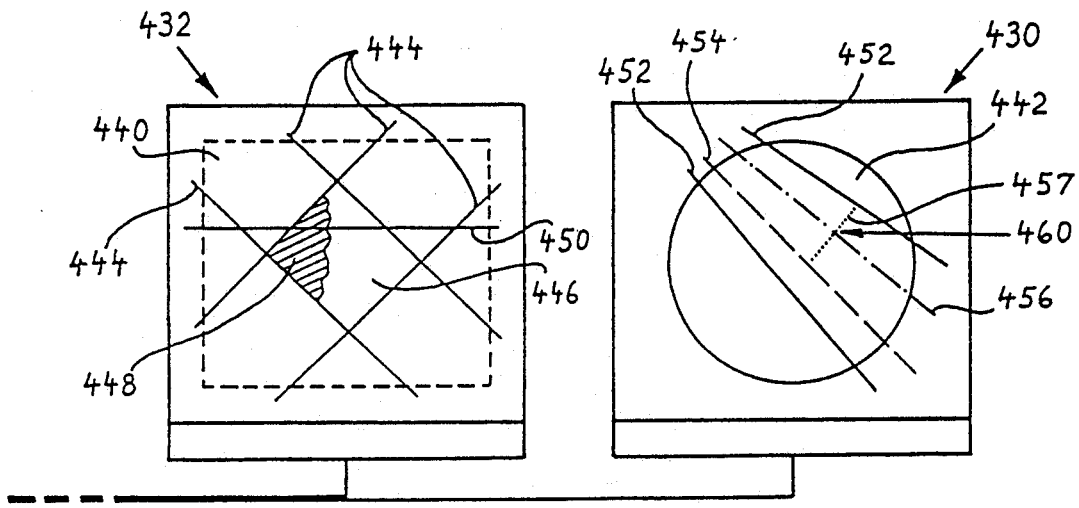
FIG. 7 is a schematic representation of an example of coordinated image displays including blocker contour projections; and, FIG. 8 is a schematic representation of another example of coordinated image displays including a plurality of tomographic views.

FIG. 7 illustrates monitors 430 and 432 that are similar or identical to monitors 24 and 26, as they are connected to computer 22 in the system shown in FIG. 1. These monitors also correspond to port image display unit 432 and tomography display unit 430 connected to computer work station 426 in FIG. 5. For clarity's sake, the following description in conjunction with FIG. 7 will employ the latter terms.

Depicted in FIG. 7 are examples of operational images to illustrate relationships between delineating lines (or wires) displayed in a planar image 440 upon the screen of port image display unit 432 and thereto coordinated beam delineators displayed in an associated tomographic image 442 upon the screen of tomography display unit 430. The arrangement shown here is similar to the arrangement illustrated in FIG. 6, except that depictions of sample planar (X-ray) image details and of associated sample tomographic image details are omitted. Instead, a rectilinear dashed outline is intented to represent the region of planar image 440 in port image display unit 432 and a circular outline is intended to represent the region of the associated tomographic image 442 in tomography display unit 430.

Four individually adjustable rectilinearly arranged field delineator lines 444 define a field 446 therebetween upon planar image 440. Not only the size and position, but also the angular orientation of field 446 are adjustable by manual computer input, for instance by appropriate operation of a mouse or light pen or another digitizer input unit (for example, digitizer unit 436 in FIG. 5).

A sample planned blocker contour projection 448 is shown imaged in field 446. A sample tomography slice plane 450 is indicated as a line imaged in planar image 440. Tomography slice plane 450 corresponds to the plane of the tomographic image 442 displayed on tomography display unit 430. Hence, it will be appreciated that the two images displayed upon units 430 and 432 are mutually orthogonal views.

Superposed over tomographic image 442 are beam delineator outlines 452 corresponding to the intersection outlines between a planned irradiation beam (as given by field 446) and the tomography slice plane 450. Further superposed over tomographic image 442 is a blocker contour ray 454 which corresponds to that ray (of the x-ray beam) that intersects the respective edge of the blocker contour projection 448 in the tomography slice plane 450. Additionally, a central beam 456 corresponds to the line joining the x-ray source point with the isocenter of the simulator apparatus (and also the isocenter of the irradiation treatment apparatus). Hence, the orientation of the central beam 456 represents the port angle. Still further superposed over tomographic image 442 is a treatment line 457 which intersects central beam 456 and, at this intersection, generally defines a treatment center 460. Treatment center 460 most often coincides with the center of the body region that is to be irradiated.

In operation of the coordinated displays shown in FIG. 7, the physician selects the position of treatment center 460, the port angle (as given by the central beam 456), and, the positions and orientation of the field delineator lines 444. Further, the physician typically draws a blocker contour (for instance contour 448 or, alternately, blocker contour ray 454) by use of a mouse, light pen, or another digitizer-input unit. As different tomography slice planes can be selected, corresponding selected different blocker contour rays provide points superposed upon planar image 440—the points being interconnected to result in a blocker contour projection (such as blocker contour projection 448 in FIG. 7).

The above-described capabilities offer uniquely advantageous convenience, accuracy, and effectiveness by facilitating irradiation planning procedures based on one or more tomographic images in correlation with a planar x-ray image. These advantages will be particularly apparent when compared with the prior general practice of relying upon substantially only on a planar x-ray image often in conjunction with a non-correlated tomographic section.

Figure 8:
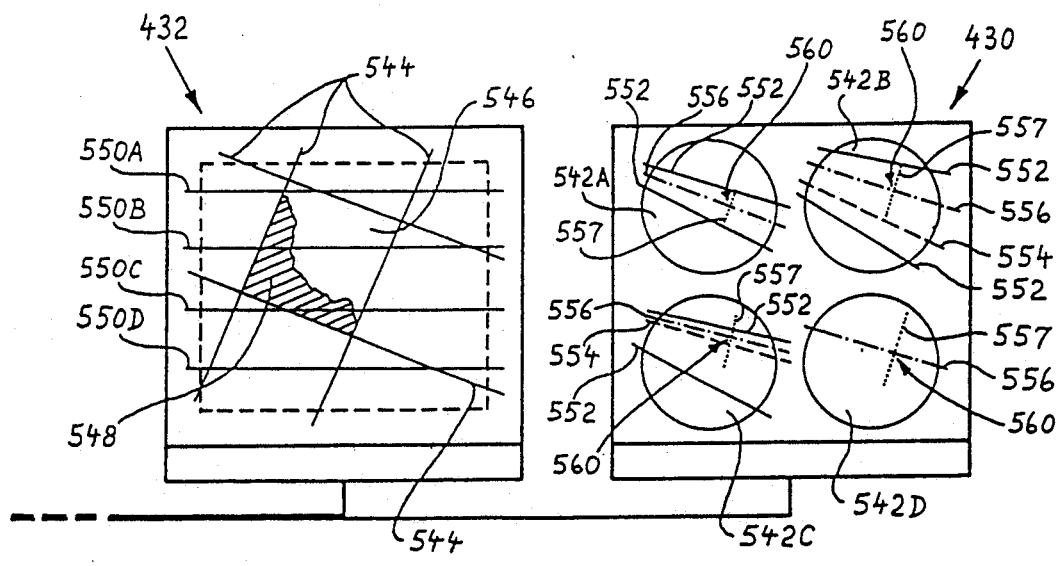

FIG. 8 also illustrates the advantageous features of the system according to the present invention. In this respect, FIG. 8 depicts another example of associated and coordinated planar and tomographic images displayable and manipulatable by a physician during planning of irradiation treatment and layout of irradiation blockers (masks). In particular, FIG. 8 shows the use of multiple tomographic views (associated and coordinated) in conjunction with a planar x-ray image. The hereinabove described capabilities are further enhanced by the features of this embodiment. FIG. 8 is identical to FIG. 7 in regard to port image display unit 432 and tomographic display unit 430, but the screen displays show different images.

The display unit 432 of FIG. 8 shows a planar (x-ray) image 540 having superposed thereover first, second, third, and fourth tomography slice planes 550A, 550B, 550C, and 550D, respectively. Field delineator lines 544 define a field 546 therebetween. Further superposed within field 546 is a sample blocker contour projection 548.

Display unit 430 shows first, second, third, and fourth coordinated tomographic images 542A, 542B, 542C, and 542D, respectively, which correspond to respective slice planes 550A, 550B, 550C, and 550D (in planar image 540). Each of the tomographic images is overlaid with a line representative of the central beam 556 (analogous to central beam 456 in FIG. 16), and further with a treatment line 557 (analogous to treatment line 457 in FIG. 7). The intersection between treatment line 557 and central beam 556 generally defines a treatment center 560 that most often coincides with the center of the body region that is to be irradiated.

Analogously to the depiction of FIG. 7, further superposed upon the tomographic images are beam-delineator outlines 552 wherever the planned beam intersects the particular tomographic slice plane (in 542A, 542B, and 542C). In this regard, the planned beam corresponds to the beam shown in planar image 540 by its cross-section or field 546). Also analogously to the depiction of FIG. 7, tomographic images are superposed by a blocker contour ray 554 wherever a tomographic slice plane intersects a planned blocker contour projection (shown here as blocker contour projection 548)—the latter being the case in tomographic images 542B and 542C.

In the above regard, it will be seen from the image shown on port image display unit 432 that only tomography slice planes 550A, 550B, and 550C intersect field 546; and, that only slice planes 550B and 550C intersect blocker contour projection 548.

The operation of the embodiment depicted in FIG. 8 is substantially the same as the operation described in conjunction with FIG. 7. An exception is that the simultaneous availability of coordinated tomographic images (and the locations of their corresponding slice planes with respect to the associated planar x-ray image 540) offers to the physician an enhanced facility for planning the irradiation process. Visualization of the anatomy and of the projection of an irradiation beam is facilitated not only in two accurately coordinated orthogonal planes, but across a plurality of coordinated planes orthogonal to the associated planar x-ray image. Thus, an accurate (to-scale) three-dimensional and in-depth picture of the treatment region is made available to the physician.

Moreover, the above-described three-dimensional picture is interactively superposed by accurate graphic information of planned (adjustable) irradiation beam geometry and of the geometric effects of a planned (adjustable) radiation blocker contour projection. The effects of the physician's selections of the geometric irradiation parameters are immediately displayed in all views and can quickly be changed and modified interactively until the physician is satisfied that the best choices have been made. A resulting blocker contour projection can be selectively displayed by itself, and is immediately convertible to appropriate blocker or blocker paragon cutting information, and a blocker or a paragon therefor can be machined immediately under control of the same computer (for instance of computer work station 426, FIG. 5).

It will be clear, in view of the foregoing, that appropriate blocker contour and irradiation beam simulations (in 3-D) can be analogously superimposed upon displayed three-dimensional, in-depth views hereinbefore discussed.

While the invention has been particularly shown and described with reference to preferred embodiments thereof, it will be understood by those skilled in the art that various changes and modifications in form and details may be made therein without departing from the spirit and scope of the invention.

The embodiments of the invention in which an exclusive property or privilege is claimed are defined as follows:

1. A system for providing planar and tomographic views of portions of a patient's anatomy, said system having an X-ray source for generating planar X-ray transmission images of portions of a patient's anatomy, said system comprising:
   computer means for acquisition and digital processing of said planar X-ray transmission images; and,
   radiation image detecting means for detecting said planar X-ray transmission images and converting said planar X-ray transmission images to planar computer-grabbable images for processing by said computer means,
   said radiation image detecting means including:

an area solid state camera for detecting light images and for providing electronic signals corresponding to said light images to said computer means, said camera having a planar array of a plurality of discrete light detectors and means for cooling thereof below ambient temperatures, said planar array comprising charge coupled devices, and means for passively converting said planar X-ray transmission images to planar light images detectable by said solid state camera, a folded optical path between said means for passively converting and said area solid state camera, said folded optical path having a mirror disposed therealong, said path being folded substantially orthogonally by said mirror, said computer means including:

means for storing, reconstructing, and visually displaying planar images detected by said area solid state camera, and means for constructing a plurality of tomographic views form planar light images that have been detected by said solid state camera during relative rotation between a patient and said radiation image detecting means and for storing, reconstructing, and visually displaying said tomographic views, each of said plurality of tomographic views being representative of a different section plane through the patient's anatomy.

2. The system according to claim 1, wherein said means for passively converting includes a phosphorescent screen.

3. The system according to claim 1, wherein is defined an iso-center axis between said X-ray source and through a center of a patient's anatomy to be imaged, said means for passively converting having an image-lane area, said iso-center axis being oriented substantially orthogonally to said image-plane area, said iso-center axis intersecting said image-plane area at a substantially central location thereof while said computer means is operative in acquiring planar images, wherein said radiation image detecting means is repositionable in relation to said X-ray source and said patient's anatomy so that said iso-center axis intersects said image-plane area at a substantially peripheral location thereof while said computer means is operative in acquiring images for constructing said tomographic views.

4. The system according to claim 1, further including:

means for rotating said X-ray source and said radiation image detecting means about a patient disposed therebetween and thereby about an axis defined through the patient; and, means for grabbing successively by said computer means a plurality of planar light images corresponding to said planar X-ray transmission images that are each obtained form a different direction while said X-ray source and said image detecting means are rotated about the patient.

5. The system of claim 4, wherein said means for constructing tomographic views include means for constructing a plurality of different tomographic views corresponding to different sections through the patient's anatomy along any desired section plane from the plurality of planar light images grabbed by said means for grabbing.

6. The system of claim 4, further including means for reconstructing three-dimensional in-depth views of portions of the patient's anatomy from the plurality of planar light images grabbed by said means for grabbing and means for visually displaying the three-dimensional in-depth views.

7. The system of claim 6, further including means for revolving the three-dimensional in-depth views about a selected axis during display thereof by said means for visually displaying.

8. A method for providing planar and tomographic views of portions of a patient's anatomy comprising the steps of:

generating planar radiation transmission images of selected portions of a patient's anatomy and projecting said planar transmission images upon an image-plane of a converter;

passively converting said planar radiation transmission images in said converter to planar light images;

detecting said planar light images by an area solid state camera and thereby converting said planar light images to electronic image signals, said step of detecting including cooling of at least an image detector portion of said area solid state camera below ambient temperatures, said converter and said area solid state camera having an optical path here between, the sep of detecting including folding said optical path substantially orthogonally by a mirror;

acquiring, processing, and storing said electronic image signals by computer means;

reconstructing planar display views form said electronic image signals by said computer means;

displaying said planar display views on visual display means of said computer means;

constructing tomographic views by said computer means from said electronic image signals that correspond to said planar light images, each of said tomographic views being representative of a different section plane through the patient's anatomy; and, displaying said tomographic views on visual display means of said computer means.

9. The method according to claim 8, wherein the step of passively converting is effected by a phosphorescent screen.

10. The method according to claim 8, further comprising a step of rotating a radiation source and a radiation image detector assembly about a patient disposed therebetween and thereby about an axis defined through said patient, wherein said step of acquiring, processing, and storing includes a step of grabbing successively a plurality of planar light images corresponding to said planar radiation transmission images that are each obtained form a different direction during said step of rotating.

11. The method of claim 10, wherein said step of constructing includes a step of constructing, form the plurality of planar light images, a plurality of different tomographic views corresponding to different sections through the patient's anatomy along section planes, one of said section planes being oriented substantially orthogonally with respect to said axis and the other said section planes having angular orientations in relation to said axis that differ only minimally or insignificantly from orthogonality.

12. The method of claim 10, wherein said step of constructing includes a step of constructing, from the plurality of planar light images, a plurality of different tomographic views corresponding to different sections through the patient's anatomy along any selected section plane.

13. The method of claim 10, further including reconstructing three-dimensional in-depth views of portions of a patient's anatomy from the plurality of planar light images, and displaying said three-dimensional in-depth views upon said visual display means.

14. The method of claim 13, wherein said step of displaying said three-dimensional in-depth views further includes revolving of said three-dimensional in-depth views about a selected axis.

15. A system for generating irradiation blockers, said system including an irradiation simulator having an X-ray source for generating planar X-ray transmission images of selected portions of a patient's anatomy, said system comprising:

computer means for acquisition and digital processing of said planar x-ray transmission images;

radiation image detecting means of detecting said planar X-ray transmission images and converting said planar X-ray transmission images to computer-grabbable images for processing by said computer means, said radiation image detecting means including:

an area solid state camera for detecting planar light images and for providing electronic signals corresponding to said planar light images to said computer means, and means for passively converting said planar X-ray transmission images to planar light images detectable by said area solid state camera; and, a folded optical path between said means for passively converting and said area solid state camera, said folded optical path having a mirror disposed therealong, said path being folded substantially orthogonally by said mirror;

said computer means including:

means for storing, reconstructing, and visually displaying said planar light images detected by said area solid state camera, means for constructing tomographic views from said planar light images detected by said area solid state camera and for storing, reconstructing, and visually displaying said tomographic views, each of said tomographic views being representative of a different section plane through the patient's anatomy, means for receiving manual inputs to superimpose blocker projection and intersection outlines thereof with said planar images an said tomographic views, respectively, upon displayed said planar display views and displayed said tomographic views, respectively, and means for generating cutter control signals form said blocker projection outlines; and, means for cutting a blocker or blocker pattern corresponding to said blocker projection outlines under control of said means for generating.

16. The system according to claim 15, wherein said solid state camera includes a planar array of a plurality of discrete light detectors.

17. The system of claim 16, wherein said solid state camera includes means for cooling said planar array below ambient temperatures.

18. The system of claim 16, wherein said planar array comprises charge coupled devices.

19. The system according to claim 15, wherein said means for passively converting includes a phosphorescent screen.

20. The system according to claim 15, wherein is defined an iso-center axis between said X-ray source and through a center of a patient's anatomy to be imaged, said means for converting having an image-plane area, said iso-center axis being oriented substantially orthogonally to said image-plane area, said iso-center axis intersecting said image-plane area at a substantially central location thereof while said computer means is operative in acquiring planar images, wherein said radiation image detecting means is repositionable in relation to said X-ray source and said patient's anatomy so that said iso-center axis intersects said image-plane area at a substantially peripheral location thereof while said computer means is operative in acquiring images for constructing said tomographic views.

21. The system according to claim 15, wherein said computer means further comprise means for producing an irradiation beam simulation and for displaying intersection outlines of said irradiation beam simulation with said planar images and with therewith associated said tomographic views that are displayed by said means for visually displaying, said intersection outlines being correlated between said planar images and said therewith associated tomographic views and being overlaid thereupon.

22. The system according to claim 15, wherein said computer means further comprise means for generating and displaying one or more tomography slice line projections superposed upon said planar image, each one of said one or more tomography slice line projections corresponding to one of said one or more tomographic views that are associated with said planar image.

23. A method of generating an irradiation blocker in the course of irradiation simulation procedures comprising the steps of:

generating planar radiation transmission images of selected portions of a patient's anatomy and projecting said transmission images upon an image-plane of a converter;

passively converting said planar radiation transmission images in said converter to planar light images;

detecting said planar light images by an area solid state camera and thereby converting said planar light images to electronic image signals, said step of detecting including cooling of at least an image detector portion of said area solid state camera below ambient temperatures, said are solid state camera and said converter having an optical path therebetween;

folding said optical path substantially orthogonally by a mirror;

acquiring, processing, and storing said electronic image signals by computer means;

reconstructing planar display views form said electronic image signals by said computer means;

displaying said planar display views on visual display means of said computer means;

constructing tomographic views from said electronic image signals by said computer means;

displaying said tomographic views on visual display means of said computer means;

receiving manual inputs of blocker information by said computer means; and, superimposing blocker projection outlines and blocker projection intersection lines upon side planar display views and upon said tomographic views, respectively, in coordinated manner under control of said computer means.

24. The method according to claim 23, further comprising the steps of:
  generating cutter control signals for cutting of blockers or blocker patterns from said blocker information by said computer means; and,
  cutting a blocker or blocker pattern under control of said cutter control signals.

25. The method according to claim 23, wherein the step of passively converting is effected by a phosphorescent screen.

26. The method according to claim 23, further comprising a step of simulating an irradiation beam, said step of simulating including:
  displaying intersection outlines of said irradiation beam with said planar images superposed thereupon; and,
  displaying intersection outlines of said irradiation beam with said tomographic views superposed thereupon.

27. A method for providing planar and tomographic views of portions of a patient's anatomy comprising the steps of:
  transmitting gradiation from a source thereof along preselected mutually coplanar radiation centerline directions through said portions of a patient's anatomy onto a planar screen of a passive image converter an thereby projecting planar radiation transmission images of said portions onto said screen, said directions intersecting centrically an axis of relative rotation between said patient's anatomy and said source together with said planar screen, said transmitting being effected substantially along an iso-center axis that intersects said planar screen orthogonally;
  passively converting said planar radiation transmission images into planar light images by said passive image converter;
  viewing and acquiring said planar light images by an area solid state camera and therein converting said planar light images to electronic image signals, said camera and said image converter having an optical path therebetween, said step of viewing and acquiring including cooling of at least an image detector portion of said area solid state camera below ambient temperatures;
  storing said electronic image signals in computer means;
  selectively reconstructing planar display views corresponding to predetermined ones of said planar light images from said electronic image signals by said computer means and displaying said planar display views; and,
  selectively constructing at least two tomographic views form said electronic image signals by said computer means and displaying said at least two tomographic views, said at least two tomographic views including one view at the plane in which said mutually coplanar radiation centerline directions are located, said at least two tomographic views including further at least one view at a plane that is substantially parallel to said plane in which said mutually coplanar radiation center line directions are located.

28. The method according to claim 27, wherein the step of viewing and acquiring is preceded by positioning said iso-center axis to intersect said planar screen at a substantially central location thereof.

29. The method according to claim 27, wherein the step of viewing and acquiring is preceded by positioning said iso-center axis to intersect said planar screen at a substantially peripheral location thereof.

30. The method according to claim 27, wherein the step of transmitting includes a step of rotating said source together with said planar screen about said axis of relative rotation; and, wherein said steps of viewing, acquiring, converting, and storing include grabbings and storing successively a plurality of sets of said electronic image signals by said computer means, each said set corresponding to a planar radiation transmission image obtained along a different one of said mutually coplanar radiation centerline directions.

31. The method of claim 30, wherein the steps of selectively reconstructing and displaying include reconstructing and displaying two mutually orthogonal planar display views corresponding to two mutually orthogonal ones of said planar light images and further constructing by said computer means and displaying and superimposing upon said two display views respective intersecting lines between said tow planar light images.

32. The method of claim 31, wherein the steps of selectively constructing and displaying at least two tomographic views include constructing and displaying superimposed upon at least one of said tomographic views respective intersection lines therebetween and said two mutually orthogonal ones of said planar light images.

* * * * *